United States Patent
Gardner et al.

(10) Patent No.: US 6,537,531 B1
(45) Date of Patent: Mar. 25, 2003

(54) HYDROLYTICALLY STABLE ESTERS

(75) Inventors: Bryce Gardner, Somerville, NJ (US);
John Imperante, Somerville, NJ (US);
Anthony J. O'Lenick, Jr., Dacula, GA (US)

(73) Assignee: Phoenix Research Corporation, Somerville, NJ (US)

( * ) Notice: Subject to any disclaimer, the term of this patent is extended or adjusted under 35 U.S.C. 154(b) by 0 days.

(21) Appl. No.: 10/039,975

(22) Filed: Jan. 8, 2002

(51) Int. Cl.[7] .................................................. A61K 7/03
(52) U.S. Cl. ........................ 424/69; 424/70.1; 554/220; 554/221
(58) Field of Search ................................. 554/220, 221; 424/69, 70.1

(56) References Cited

U.S. PATENT DOCUMENTS 5,488,121 A    1/1996    O'Lenick

Primary Examiner—Deborah D. Carr

(57) ABSTRACT

The present invention deals with the certain novel esters derived from a specific 36 carbon diol and guerbet acids, which unlike other esters are surprisingly stable to hydrolysis and consequently of interest in high and low pH applications.

16 Claims, No Drawings

HYDROLYTICALLY STABLE ESTERS

BACKGROUND OF THE INVENTION

1. Field of the Invention

The present invention deals with the certain novel esters derived from a specific 36 carbon diol and guerbet acids, which unlike other esters are surprisingly stable to hydrolysis and consequently of interest in high and low pH applications.

2. Description of the Art Practices

Guerbet alcohols have been known for many years, primarily for their liquidity at high molecular weight. Over the years there have been a number of derivatives patented.

U.S. Pat. No. 4,868,236 to O'Lenick discloses a guerbet citric ester and polymers thereof useful in plastic lubrication.

U.S. Pat. No. 5,488,121 issued Jan. 30, 1996 to O'Lenick teaches that esters based upon a guerbet acid and guerbet alcohol have surprisingly good liquidity.

All of these materials are subject to hydrolysis, a retrograde reaction in which water breaks down the ester into the starting materials. The rate of hydrolysis in esters is directly related to pH, limiting their usefulness to pH below 10 and above 5. Unfortunately, there are a number of cosmetic applications in which both conditions of pH are commonly encountered. There include hair treatments, including relaxers (pH 13) and hydroxy acid formulations (pH below 5). The compositions of the present invention unlike standard esters are stable at these pH values. Consequently, they can be used to provide conditioning, emmoliency, and barrier properties to hair and skin at these high and low pH values.

THE INVENTION

Objective of the Invention

It is the objective of the present invention to provide novel ester compositions, based upon (a) specific branched guerbet acids and (b) a novel dimer alcohol, which when both present in the same molecule result in an ester that exhibits outstanding stability at high and low pH values, heretofore unattainable.

It is another objective of the present invention to provide a process for conditioning hair and skin using formulations having a pH below 5 or above 10 using said novel ester compositions, based upon (a) specific branched guerbet acids and (b) a novel dimer alcohol.

Other objectives will become apparent reading the present teachings.

SUMMARY OF THE INVENTION

The compositions of the current invention conform to the following formulae;

$$R-O-C(O)-(CH_2)_7-CH(-(CH_2)_8-CH_3)-$$
$$R-O-C(O)-(CH_2)_7-CH(-(CH_2)_8-CH_3)-$$

[Cyclohexane-based structures with R—O—C(O)—(CH$_2$)$_7$— substituents and CH—(CH$_2$)$_7$—CH$_3$, HC—(CH$_2$)$_5$—CH$_3$ branches]

[Additional structures with RO(O)C(CH$_2$)$_7$—, H—O—C(O)—(CH$_2$)$_7$—, and HO(O)C(CH$_2$)$_7$— variants on cyclohexane rings with (CH$_2$)$_7$—CH$_3$ and (CH$_2$)$_5$—CH$_3$ branches]

[Aromatic ring structures with H—O—C(O)—(CH$_2$)$_7$—C substituents bearing CH—(CH$_2$)$_7$—CH$_3$ and C—(CH$_2$)$_5$—CH$_3$ branches] and with a guerbet acid conforming to the following structure; and

[Aromatic ring structure with R—O—C(O)—(CH$_2$)$_7$—C substituents bearing CH—(CH$_2$)$_7$—CH$_3$ and C—(CH$_2$)$_5$—CH$_3$ branches]

wherein;

R is $$(CH_2)_b-CH_3$$
$$CH_3-(CH_2)_a-CH-CH_2-$$

wherein
a, b, are independently integers ranging from 4 to 18.

DETAILED DESCRIPTION OF THE INVENTION

The compositions of the present invention are made by the esterification of a dimer dimol diacid conforming to the following structure:

$$H-O-C(O)-(CH_2)_7-CH(-(CH_2)_8-CH_3)-$$
$$H-O-C(O)-(CH_2)_7-CH(-(CH_2)_8-CH_3)-$$

$$(CH_2)_b-CH_3$$
$$CH_3-(CH_2)_a-CH-C(O)-OH$$

wherein;
a, b, are independently integers ranging from 4 to 18.

Another aspect of the present invention is a process for conditioning hair and skin, which comprises contacting the hair or skin with an effective conditioning concentration of a composition conforming to the following formula;

$$R-O-C(O)-(CH_2)_7-CH(-(CH_2)_8-CH_3)-$$
$$R-O-C(O)-(CH_2)_7-CH(-(CH_2)_8-CH_3)-$$

-continued $$R-O-C(O)-(CH_2)_7-CH\overset{CH-(CH_2)_7-CH_3}{\underset{CH_2}{\overset{|}{\underset{|}{C}H}}}\overset{HC-(CH_2)_5-CH_3}{\underset{CH_2}{\overset{|}{C}H_2}}$$

$$\text{RO(O)C(CH}_2)_7-CH \quad CH_2$$
$$\text{RO(O)C(CH}_2)_7-CH \quad CH \quad HC-(CH_2)_5-CH_3 \quad \text{and}$$
$$CH_2 \quad CH \quad HC-(CH_2)_5-CH_3$$
$$CH_2 \quad CH_2$$

$$R-O-C(O)-(CH_2)_7-C\overset{CH-(CH_2)_7-CH_3}{\underset{CH}{\overset{|}{C}}}\overset{C-(CH_2)_5-CH_3}{\underset{CH}{\overset{|}{C}H}}$$
$$R-O-C(O)-(CH_2)_7-C\overset{}{\underset{CH}{\overset{|}{C}}}CH$$

wherein; R is; $CH_3-(CH_2)_a-CH\overset{(CH_2)_b-CH_3}{\underset{}{\overset{\diagdown}{}}}$ a, b, are independently integers ranging from 4 to 18.

Preferred Embodiments

In a preferred embodiment a is 5 and b is 3.

In a preferred embodiment a is 7 and b is 5.

In a preferred embodiment a is 9 and b is 7.

In a preferred embodiment a is 11 and b is 9.

In a preferred embodiment a is 13 and b is 11.

In a preferred embodiment a is 17 and b is 15.

In a preferred embodiment a is 19 and b is 17.

In a preferred embodiment, the effective conditioning concentration ranges from 0.1 to 20% by weight.

In a preferred embodiment, the effective conditioning concentration ranges from 1 to 10% by weight.

EXAMPLES

Raw Materials

Dimer Dimol Alcohol

Dimer dimol alcohol is a composition of the following components, commercially available from Jarchem Industries Inc Newark, N.J. It conforms to the following formulae:

$$H-O-C(O)-(CH_2)_7-CH-(CH_2)_8-CH_3$$
$$H-O-C(O)-(CH_2)_7-CH-(CH_2)_8-CH_3$$

$$H-O-C(O)-(CH_2)_7-CH\overset{CH-(CH_2)_7-CH_3}{\underset{CH_2}{\overset{|}{\underset{|}{C}H}}}\overset{HC-(CH_2)_5-CH_3}{\underset{CH_2}{\overset{|}{C}H_2}}$$

$$\text{HO(O)C(CH}_2)_7-CH \quad CH_2$$
$$\text{HO(O)C(CH}_2)_7-CH \quad CH \quad HC-(CH_2)_5-CH_3 \quad \text{and}$$
$$CH_2 \quad CH \quad HC-(CH_2)_5-CH_3$$
$$CH_2 \quad CH_2$$

$$H-O-C(O)-(CH_2)_7-C\overset{CH-(CH_2)_7-CH_3}{\underset{CH}{\overset{|}{C}}}\overset{C-(CH_2)_5-CH_3}{\underset{CH}{\overset{|}{C}H}}$$
$$H-O-C(O)-(CH_2)_7-C\overset{}{\underset{CH}{\overset{|}{C}}}CH$$

Guerbet Acids

Guerbet alcohols are oxidized into acids having the same regiospecific beta branched properties.

$$CH_3-(CH_2)_a-CH\overset{(CH_2)_b-CH_3}{\underset{CH_2-O-H}{\overset{|}{}}} \xrightarrow{\text{oxidized}}$$

Guerbet Alcohol $$CH_3-(CH_2)_a-CH\overset{(CH_2)_b-CH_3}{\underset{C(O)-OH}{\overset{|}{}}}$$

Guerbet Acid

Condea Chemical practices the oxidation of guerbet alcohols commercially. The values of a and b were actually determined by analysis and are not dependant upon trade name for meaning.

| Example | Commercial Name | a | b | Chemical Name |
|---|---|---|---|---|
| 1 | Isocarb 12 | 5 | 3 | 2-butyl-octanol |
| 2 | Isocarb 16 | 7 | 5 | 2-hexyl-decanol |
| 3 | Isocarb 20 | 9 | 7 | 2-octyl-dodecanol |
| 4 | Isocarb 24 | 11 | 9 | 2-decyl-tetradecanol |
| 5 | Isocarb 28 | 13 | 11 | 2-dodecyl-hexadecanol |
| 6 | Isocarb 36 | 17 | 15 | 2-hexadecyl-eicosonal |

Isocarb is a trademark of Condea Vista.

Ester Synthesis

The esterification reaction is carried out using an excess of dimol or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure

To 261.0 grams of dimer dimol alcohol is added the specified number of grams of the specified guerbet acid (Examples 1–6). Next add 0.1% stannous oxylate based upon the total weight of the batch after all ingredients have been charged, under agitation. The temperature of the mass is raised to 180–200° C. and water is stripped off as formed. The acid value and hydroxyl value drop to vanishingly small values.

| | Guerbet Acid | |
|---|---|---|
| Example | Example | Grams |
| 7 | 1 | 186.0 |
| 8 | 2 | 242.0 |
| 9 | 3 | 298.0 |
| 10 | 4 | 354.0 |
| 11 | 5 | 410.0 |
| 12 | 6 | 522.0 |

APPLICATIONS EXAMPLES

All products show an extraordinary resistance to hydrolysis both on the acidic and alkaline pH values. This is most easily seen when one attempts to run a saponification value. Saponification value is an analytical technique, which allows one to determine the molecular weight of an ester, by breaking down the ester with base (KOH). In standard esters, the amount of KOH consumed in the analysis is measured and is stiochiometric with the molecular weight of the ester. Surprisingly, the esters of the present invention do not have the expected saponification value. They have essentially no saponification value, since the ester must hydrolyze to provide the saponification value.

Saponification Analysis

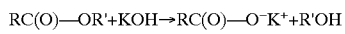
$RC(O)—OR'+KOH \rightarrow RC(O)—O^-K^+ +R'OH$

The analysis is run with excess KOH and the difference between the starting amount of KOH and the residual KOH is titrated with standardized acid. The amount of KOH consumed is stiochiometric and the saponification value is reported as mg KOH/gram of sample tested.

Saponification Value Method

This method is applicable to all fats and oils, as well as products derived from them such as esters and fatty acids. The saponification value is the amount of alkali necessary to saponify a definite quantity of the sample. It is expressed as the number of milligrams of potassium hydroxide (KOH) required to saponify one gram of the sample. A sample is refluxed in 0.5N methanolic KOH for 1.5 hours and titrated using 0.5N HCl.

Materials needed are:
1. Potassium hydroxide (KOH), ethanolic 0.5N
2. Hydrochloric acid (HCl), 0.5N
3. Phenolphthalein indicator solution, 0.1% in ethanol.

Procedure:
1. Melt the sample, if not a liquid, and mix thoroughly to ensure homogeneity. Using Table 1 as a guide, weigh the appropriate amount of sample into an Erlenmeyer flask. Record the weight.
2. Pipette 50 mL of 0.5N KOH into the flask, add some boiling stones, and reflux for 1.5 hours. Make sure that there is cold water going through the condensers so as to aid in the condensing of the sample back into the Erlenmeyer flasks.
3. Prepare and run a blank simultaneously with the samples by pipetting 50 ml of 0.5N KOH into an empty flask, adding some boiling stones, and refluxing along side the samples.
4. After 1.5 hours of refluxing, rinse the inside of the condensers with about 25 mL of deionized water and catch the rinsings in the Erlenmeyer flasks. Remove the flasks from the condensers and allow the sample solutions to cool to room temperature.
5. To each flask, add 3 to 5 drops of phenolphthalein indicator and a stir bar. Titrate, while mixing, with 0.5N HCl until the pink color just disappears. Record the respective titration volumes used to reach each endpoint.
6. Using Equation 1 in the Calculations section of this method, calculate the SAP value of the samples analyzed. Report the results to one decimal place.
7. The ester value of a product can be determined using Equation 2, if the acid value is also known.

Calculations: Equation 1

$$\text{SAP value} = \frac{(\text{mL Blank} - \text{mL Sample})(N \text{ of HCl})(56.1)}{(\text{wt. of sample})}$$

Equation 2

Ester value=Saponification value–Acid value

Precision: The relative standard deviation for saponification value determinations has been determined to be ±0.5% when one sample was analyzed 36 times by different chemists on different days within the same laboratory. This relative standard deviation was determined on a sample with an average saponification value of 336.0.

Reference: A.O.C.S. Official Method Cd 3c-91.

Hydrolytic Stability of Dimer Diol Di-Guerbet Acid Esters

| PRODUCT | # CARBONS | THEORETICAL VALUE | Observed RESULT | % Hydrolyzed |
|---|---|---|---|---|
| Example 7 | 60 | 124 | 6.2 | 5.0% |
| Example 10 | 84 | 90 | 0.3 | 0.3% |
| Example 12 | 100 | 77 | 2.6 | 3.3% |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A composition conforming to the following formula;

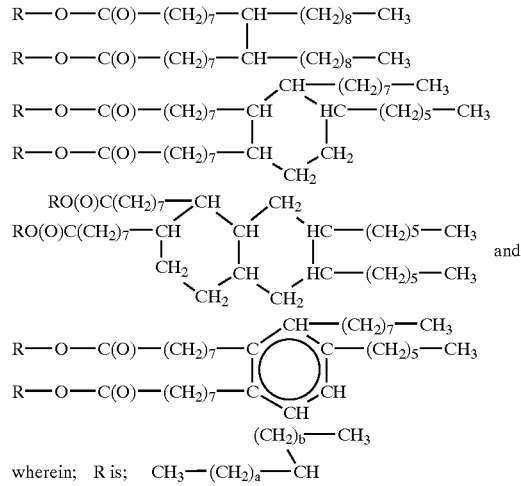

wherein; R is: $CH_3—(CH_2)_a—CH\begin{smallmatrix}\\ \diagdown\\(CH_2)_b—CH_3\end{smallmatrix}$ a, b, are independently integers ranging from 4 to 18.

2. A composition of claim 1 wherein a is 5 and b is 3.
3. A composition of claim 1 wherein a is 7 and b is 5.
4. A composition of claim 1 wherein a is 9 and b is 7.
5. A composition of claim 1 wherein a is 1 and b is 9.
6. A composition of claim 1 wherein a is 13 and b is 11.
7. A composition of claim 1 wherein a is 17 and b is 15.
8. A composition of claim 1 wherein a is 18 and b is 16.
9. A process for conditioning hair and skin, which comprises contacting the hair or skin with an effective conditioning concentration of a composition conforming to the following formula;

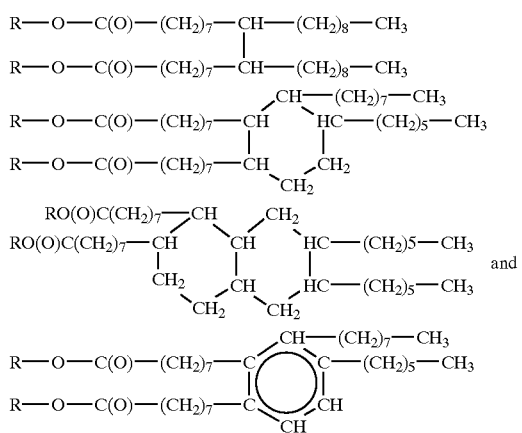

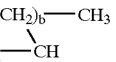

wherein; R is;

a, b, are independently integers ranging from 4 to 18.

10. A process of claim 9 wherein the effective conditioning concentration ranges from 0.1 to 20% by weight.

11. A process of claim 10 wherein a is 5 and b is 3.

12. A process of claim 10 wherein a is 7 and b is 5.

13. A process of claim 10 wherein a is 9 and b is 7.

14. A process of claim 10 wherein a is 11 and b is 9.

15. A process of claim 10 wherein a is 12 and b is 11.

16. A process of claim 10 wherein a is 17 and b is 15.

* * * * *